United States Patent
Huang et al.

(10) Patent No.: US 10,258,557 B2
(45) Date of Patent: Apr. 16, 2019

(54) PEPTIDE FOR STIMULATING MELANOGENESIS

(71) Applicant: Yu-Chun Liu, Taoyuan (TW)

(72) Inventors: Min-Chuan Huang, Taipei (TW); Syue-Ting Chen, Taipei (TW); Yu-Chun Liu, Taoyuan (TW)

(73) Assignee: Yu-Chun Liu, Taoyuan (TW)

( * ) Notice: Subject to any disclaimer, the term of this patent is extended or adjusted under 35 U.S.C. 154(b) by 0 days.

(21) Appl. No.: 15/626,891

(22) Filed: Jun. 19, 2017

(65) Prior Publication Data

US 2018/0360721 A1    Dec. 20, 2018

(51) Int. Cl.

| | | |
|---|---|---|
| *A61K 38/02* | (2006.01) | |
| *A61K 38/17* | (2006.01) | |
| *A61K 8/64* | (2006.01) | |
| *A61K 8/98* | (2006.01) | |
| *C07K 7/06* | (2006.01) | |
| *C07K 7/00* | (2006.01) | |
| *A61Q 7/00* | (2006.01) | |
| *A61Q 5/02* | (2006.01) | |
| *A61Q 5/10* | (2006.01) | |
| *A61Q 5/12* | (2006.01) | |

(52) U.S. Cl.
CPC .................. *A61K 8/64* (2013.01); *A61Q 5/02* (2013.01); *A61Q 5/10* (2013.01); *A61Q 5/12* (2013.01); *C07K 7/06* (2013.01); *A61K 2800/78* (2013.01)

(58) Field of Classification Search
CPC .......... A61K 38/02; A61K 8/64; A61K 38/17; A61K 8/98; C07K 7/06; C07K 7/00; A61Q 7/00; A61Q 5/02; A61Q 5/10
USPC ........................ 530/300, 329; 514/20.7, 21.7
See application file for complete search history.

(56) References Cited

U.S. PATENT DOCUMENTS 6,913,919 B2 * 7/2005 Botstein ............... C07K 14/705
435/252.3

OTHER PUBLICATIONS

A0A059DCJ9 from UniProt, pp. 1-3. Integrated into UniProtKB/TrEMBL Jul. 9, 2014.*
Eucalyptus Benefits from https://www.100percentpure.com/blogs/feed/eucalyptus-benefits, pp. 1-8. Accessed Dec. 11, 2018.*

* cited by examiner

*Primary Examiner* — Julie Ha
(74) *Attorney, Agent, or Firm* — Birch, Stewart, Kolasch & Birch, LLP

(57) ABSTRACT

A synthetic peptide for stimulating melanogenesis is provided. The synthetic peptide consists of the amino acid sequence of AsnSerAlaThrGluArgGlu (SEQ ID NO: 1). Also provided are methods and compositions for stimulating melanogenesis in a subject.

5 Claims, 3 Drawing Sheets
Specification includes a Sequence Listing.

24 h 48 h

```
SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Asn Ser Ala Thr Glu Arg Glu
1               5
```

PEPTIDE FOR STIMULATING MELANOGENESIS

FIELD OF THE INVENTION

The present invention relates generally to a synthetic peptide for increasing melanogenesis or increasing the melanin level in melanocytes, and compositions thereof.

REFERENCE TO SEQUENCE LISTING SUBMITTED VIA EFS-WEB

This application includes an electronically submitted sequence listing in .txt format. The .txt file contains a sequence listing entitled "2017-09-07 SequenceListing 5992-0166PUS1.txt" created on Sep. 6, 2017 and is 408 bytes in size. The sequence listing contained in this .txt file is part of the specification and is hereby incorporated by reference herein in its entirety.

BACKGROUND OF THE INVENTION

Hair color is determined by the relative amounts of the brown-black pigment eumelanin and the red-yellow pigment pheomelanin in follicular melanocytes. Increasing melanogenesis leads to increasing the melanin level in melanocytes, and hence results in increased pigmentation or darkened color of the skin, hair wool or fur.

U.S. Pat. No. 5,352,440 is directed to a method for increasing melanin synthesis in melanocytes and increasing pigmentation by administration of certain diacylglycerol compounds. U.S. Pat. No. 5,532,001 is directed to a method for increasing pigmentation in mammalian skin via administration of certain DNA fragments. U.S. Pat. No. 5,554,359 is directed to a method for increasing the melanin level in melanocytes by administration of lysosomotropic agents.

Although some efforts have been made to improve the melanin synthesis, there is still a need for compositions and methods for stimulating melanogenesis.

BRIEF SUMMARY OF THE INVENTION

It is unexpectedly found in the present invention that a newly synthesized peptide having a sequence of AsnSerAlaThrGluArgGlu (SEQ ID NO: 1) is effective in stimulating melanogenesis.

Accordingly, the present invention provides in one aspect a peptide for stimulating melanogenesis or increasing the melanin level in melanocytes. The peptide is a synthetic peptide consisting of the amino acid sequence of SEQ ID NO: 1.

In another aspect, the present invention features a method for darkening the hair color in a subject, which comprises administering to said subject the peptide according to the present invention in an amount effective to stimulate melanogenesis or to increase the melanin level in melanocytes in said subject.

In an embodiment of the invention, the melanin level in melanocytes can be increased through the stimulation of melanogenesis by the peptide according to the present invention. In one example of the invention, the peptide of the present invention can be used to darken the hair color of a subject, such as a human subject, wherein the peptide is administered topically to the subject.

In one further aspect, the present invention provides a composition for increasing the melanin level in melanocytes. The composition comprises an effective amount of the peptide having the amino acid sequence of SEQ ID NO: 1 in an amount effective to stimulate melanogenesis. In certain embodiments of the invention, the composition further comprises a physiologically acceptable carrier, and may be formulated as a topical formulation.

According to the present invention, the topical formulation may comprise an ointment, lotion, cream, gel, drops, spray, liquid, shampoo or hair conditioner. In one preferred embodiment, the composition is formulated as a shampoo or a hair conditioner.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings.

In the drawings.

DETAILED DESCRIPTION OF THE INVENTION

Figure 1A:
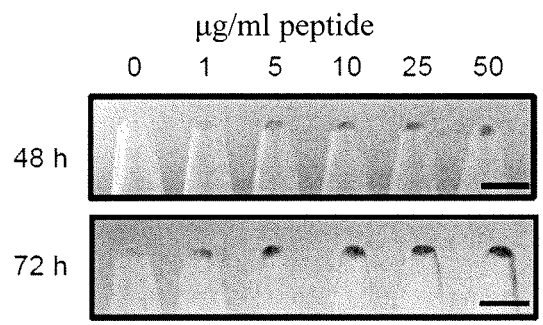
FIG. 1A provides the images of the cell pellets of B16F10 melanoma cells after treatment with the peptide having the amino acid sequence of SEQ ID NO: 1 at the various doses for 48 or 72 hours (scale bars=1 cm).

In one aspect, the present invention features a peptide for stimulating melanogenesis. The peptide is a synthetic peptide consisting of the amino acid sequence of AsnSerAlaThrGluArgGlu (SEQ ID NO: 1).

In one embodiment of the invention, the peptide is effective in increasing the melanin level in melanocytes In another aspect, the invention provides a method for darkening the hair color in a subject, which comprises administering to said subject the peptide having the amino acid sequence of SEQ ID NO: 1 in an amount effective to stimulate melanogenesis or to increase the melanin level in melanocytes in said subject.

In one example of the method according to the present invention, the peptide is administered to the subject topically.

In yet another aspect, the present invention provides a composition for increasing the melanin level in melanocytes, comprising an effective amount of the peptide having the amino acid sequence of SEQ ID NO: 1. The composition is effective in stimulating melanogenesis. The composition may be used for cosmetic purposes, for example, darkening hair color.

In certain embodiments of the invention, the composition further comprises a physiologically acceptable carrier.

In one example of the invention, the composition is formulated as a topical formulation.

Unless defined otherwise, all technical and scientific terms used herein have the same meaning as commonly understood by those of ordinary skill in the art to which this invention belongs.

The use of the word "a" or "an" when used in conjunction with the term "comprising" in the claims and/or the specification may mean "one," but it is also consistent with the meaning of "one or more," "at least one," and "one or more than one."

The term "peptide" is used herein in its conventional sense, i.e., a polymer in which the monomers are amino acids and are joined together through amide bonds, alternatively referred to as a polypeptide. When the amino acids are α-amino acids, either the L-optical isomer or the D-optical isomer may be used. Additionally, unnatural amino acids, for example, β-alanine, phenylglycine and homoarginine are also meant to be included. Standard abbreviations for amino acids are used.

As used herein, the term "subject" refers to a vertebrate, preferably a mammal, particularly preferably a human. Hereinafter, a human serving as a subject is specifically referred to as a "human subject."

As used herein, the term "carrier" refers to materials commonly used on the formulation of pharmaceutical or cosmetic composition used to enhance stability, sterility and deliverability. When the peptide delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. The compositions may contain physiologically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The term "topical" or "topically" is used herein its conventional sense as referring to a spot which can be in or on any part of the body, including but not limited to the epidermis, any other dermis, or any other body tissue. Topical administration or application means the direct contact of the peptide with tissue, such as skin or membrane which contains melanin-producing cells.

The present invention contemplates the use of the peptide having the amino acid sequence of SEQ ID NO: 1 as an active ingredient for various uses. In one embodiment, the peptide of the present invention is combined with an acceptable carrier to form a topical formulation which may be placed on the hair or skin. Topical formulations may comprise an ointment, lotion, paste, cream, gel, drop, suppository, spray, liquid, shampoo, hair conditioner, powder and transdermal patch. Thickeners, diluents, emulsifiers, dispersing aids or binders may be used as needed. Preferably, one function of the carrier is to enhance skin penetration of the peptide of the present invention, and should be capable of delivering the peptide to melanocytes under in vivo conditions. Suitable carriers are well known to one of ordinary skill, and include but are not limited to water, dimethylsulfoxide, ethanol, liposome, liquid petrolatum, petrolatum dimethylformamide, 2-pyrrolidone, oleic acid, and Azone® brand penetration enhancer.

The present invention is further illustrated by the following examples, which are provided for the purpose of demonstration rather than limitation.

EXAMPLES

Example 1: Preparation of the Peptide of SEQ ID NO: 1

The peptide having the amino acid sequence of SEQ ID NO: 1 (AsnSerAlaThrGluArgGlu) was synthesized by MDBio, Inc. (Taipei, Taiwan) and the purity and composition of peptide was confirmed by high performance liquid chromatography (HPLC) and mass spectrometry. The peptide stock was stored at −20° C. after dissolving 10 mg of lyophilized peptide powder in 500 µl of double deionized water ($ddH_2O$).

Example 2: Cell Cultures

B16F10 is a melanoma cell line isolated from mouse skin (American Type Culture Collection, USA) and was cultured in phenol red-free Dulbecco's Modified Eagle Medium (DMEM) containing 10% (v/v) FBS and penicillin/streptomycin (100 IU/50 g/ml) in 5% $CO_2$ at 37° C.

Example 3: Melanin Level Assay

The B16F10 cells ($2 \times 10^4$) were seeded into 6-well culture plates and incubated overnight. The cells were treated with different concentrations of the peptide of SEQ ID NO: 1 for 48 hours or 72 hours and then trypsinized. After photographing cell pellets in an Eppendorf tube, the cells were lysed in 1 N NaOH at 80° C. for 30 minutes. The melanin level was analyzed by a comparison of absorbance at 405 nm of tested samples with a standard curve obtained using synthetic melanin. The results were shown as means±SE pg/cell from three independent experiments.

Figure 1B:
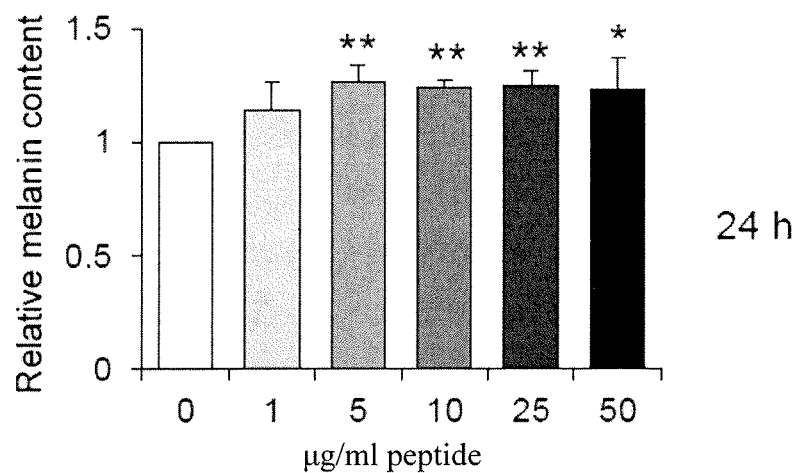
FIG. 1B shows the melanin levels as measured by spectrophotometry at wavelength 450 nm; wherein the results indicated the fold change in the melanin levels in the cells treated with the peptide having the amino acid sequence of SEQ ID NO: 1 for 24 hours (upper panel) and 48 hours (lower panel), and the melanin level in the cells treated with $ddH_2O$ without the peptide having the amino acid sequence of SEQ ID NO: 1 was 1 and the statistic results were obtained from three independent experiments. (* P<0.05; **P<0.01. shows the hyper pigmentation by the peptide of the invention in cells).
Figure 1B:
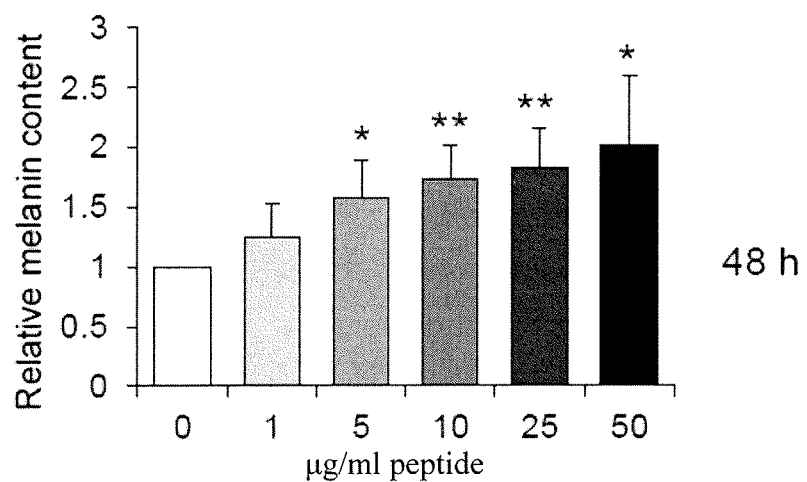

The results were shown in FIGS. 1A and 1B. It was found that the peptide of SEQ ID NO: 1 significantly increased melanin synthesis in a concentration-dependent manner (see FIGS. 1A and 1B).

Example 4: Tyrosinase Assay

The B16F10 cells ($2 \times 10^4$) were seeded into 6-well culture plates and incubated for overnight. The cells were treated with the peptide of SEQ ID NO: 1 at different concentrations for 48 hours or 72 hours and then trypsinized. The cell pellets were resuspended with phosphate buffer (pH 6.8) containing 1% Triton X-100 and incubated at 80° C. for 60 minutes. The cell debris was removed by centrifugation at 14000 rpm for 10 minutes and the protein contents were measured using the Bradford protein assay dye (Bio-Rad). For reactions, 100 µg of cell lysates were added into 200 µl of 2.5 mM L-DOPA and then incubated at 37° C. for 20 minutes. The absorbance was measured by spectrophotometry at 490 nm.

Figure 2:
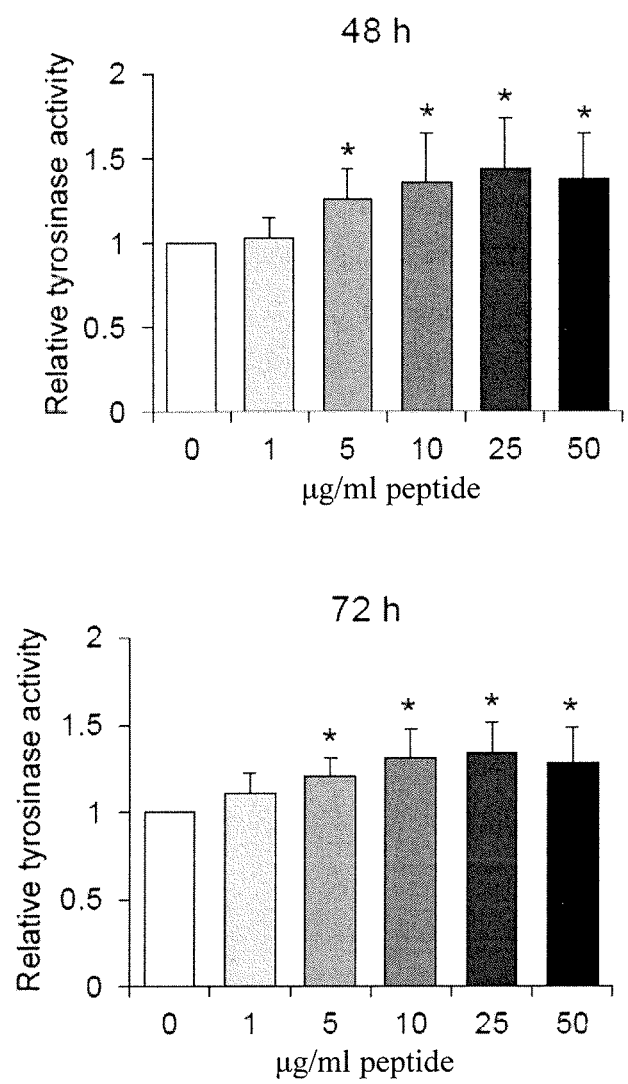
FIG. 2 shows that the peptide of SEQ ID NO: 1 increased tyrosinase activity in B16F10 cells; wherein the B16F10 cells were treated with different concentrations of the peptide having the amino acid sequence of SEQ ID NO: 1 (also called as "NO.11 peptide"), as indicated, for 48 hours (upper panel) or 72 hours (lower panel), and the cell lysates were used to analyze tyrosinase activity, and the results showed fold changes in the tyrosinase activity from three independent experiments (*P<0.05).

The results were shown in FIG. 2. It was found that the cells treated with the peptide of SEQ ID NO: 1 in the amount of 5-50 µg/ml showed significantly increased tyrosinase activity Example 5: MTT Assay The cells ($2 \times 10^3$) in 100 µl complete DMEM were seeded in 96-well plates and treated with the peptide of SEQ ID NO: 1 at different concentrations. The cells treated with $ddH_2O$ was used as controls. Ten microliters of 5 mg/ml 3-(4,5-dimethyl-2-thiazolyl)-2,5-diphenyl-2H-tetrazolium bromide solution (MTT; Sigma) was added to each well and incubated at 37° C. for 3 hours. After that, 100 µl 10% SDS in 0.01N HCl was added to dissolve the MTT formazan crystals. The resultant optical density was measured by spectrophotometry at dual wavelengths, 550 and 630 nm.

Figure 3:
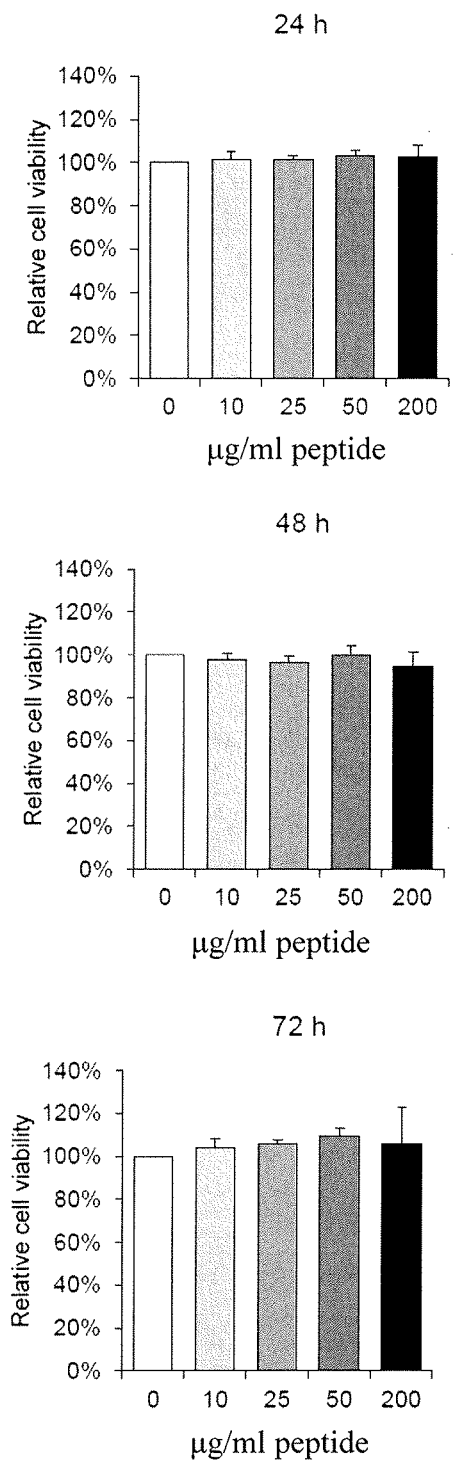
FIG. 3 shows that the peptide having the amino acid sequence of SEQ ID NO: 1 did not significantly affect viability of B16F10; wherein the B16F10 cells were treated with the peptide having the amino acid sequence of SEQ ID NO: 1 at different concentrations for 24 hours (upper panel), 48 hours (middle panel), or 72 hours (lower panel), respectively; the cell viability was analyzed by MTT assays and the results were obtained from three independent experiments.

The cell viability levels of the cells treated with the peptide of SEQ ID NO: 1 for 24 hours (upper panel), 48 hours (middle panel), or 72 hours (lower panel) were shown in FIG. 3. It was found that the peptide of SEQ ID NO: 1 did not significantly affect the viability of the B16F10 cells. Given the above, it is indicated that the peptide of SEQ ID NO: 1 is indeed able to stimulate melanogenesis, and to increase the melanin level in melanocytes in a subject, but which is not caused by the improvement in viability of the B16F10 cells It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A composition for increasing the melanin level in melanocytes, comprising
    an effective amount of a peptide consisting of the amino acid sequence of SEQ ID NO:1,
    wherein the composition is formulated as a topical formulation, and
    wherein the topical formulation comprises an ointment, lotion, cream, gel, shampoo or hair conditioner.

2. The composition of claim 1, further comprising a physiologically acceptable carrier.

3. The composition of claim 1, wherein the topical formulation is a shampoo.

4. The composition of claim 1, wherein the topical formulation is a hair conditioner.

5. A method for darkening the hair color in a subject, which comprises
    topically administering to said subject the composition of claim 1 in an amount effective to stimulate melanogenesis or to increase the melanin level in melanocytes in said subject.

* * * * *